United States Patent
Immordino, Jr. et al.

(10) Patent No.: US 8,642,346 B2
(45) Date of Patent: Feb. 4, 2014

(54) TAGGED JOINT COMPOUND AND METHOD OF IDENTIFICATION

(75) Inventors: Salvatore C. Immordino, Jr., Trevor, WI (US); Brett R. Link, Algonquin, IL (US); Charles J. Miller, Johnsburg, IL (US); Guy L. Rosenthal, Wheaton, IL (US); Richard B. Stevens, Crystal Lake, IL (US); Lee K. Yeung, Vernon Hills, IL (US)

(73) Assignee: United States Gypsum Company, Chicago, IL (US)

( * ) Notice: Subject to any disclaimer, the term of this patent is extended or adjusted under 35 U.S.C. 154(b) by 135 days.

(21) Appl. No.: 13/150,918

(22) Filed: Jun. 1, 2011

(65) Prior Publication Data

US 2012/0171772 A1    Jul. 5, 2012

Related U.S. Application Data

(60) Provisional application No. 61/428,026, filed on Dec. 29, 2010.

(51) Int. Cl.
*G01N 37/00* (2006.01)
(52) U.S. Cl.
USPC ............... 436/56; 106/35; 106/640; 106/772; 106/773; 250/282; 250/340
(58) Field of Classification Search
None
See application file for complete search history.

(56) References Cited

U.S. PATENT DOCUMENTS

| | | |
|---|---|---|
| 6,673,437 B2 | 1/2004 | Kohla et al. |
| 6,899,827 B2 | 5/2005 | Lauf et al. |
| 2004/0209376 A1 | 10/2004 | Natan et al. |
| 2005/0032226 A1 | 2/2005 | Natan |
| 2008/0315163 A1 | 12/2008 | Schroer et al. |
| 2009/0148814 A1 | 6/2009 | Li et al. |

FOREIGN PATENT DOCUMENTS

WO    WO 2005/113468    12/2005

OTHER PUBLICATIONS

Tesk, J.A., et al. Dental Material, 2002, Kirk-Othmer Encyclopedia of Chemical Technology, vol. 8, pp. 274-354.*

* cited by examiner

*Primary Examiner* — Robert Xu
(74) *Attorney, Agent, or Firm* — Greer, Burns & Crain, Ltd.; Pradip Sahu; Philip T. Petti

(57) ABSTRACT

At least one of these or other problems is reduced using a building material that is uniquely identifiable. A method of making an identifiable gypsum-based building product includes selecting a tagging material occurring naturally in a component of the building material and choosing a carrier substance having a high concentration of the tagging material. By selecting an amount of the carrier substance and adding it to the building material, a building product having a unique product characteristic is created. In a second embodiment of the invention, a second tagging material is combined with the first tagging material to create a unique product. In yet another embodiment of the invention, a supplemental amount of the tagging material is added to the gypsum-based composition in addition to the carrier substance. Some tagging materials are useful in a gypsum-based composition to produce a visual confirmation of the presence of the tagging material.

8 Claims, No Drawings

TAGGED JOINT COMPOUND AND METHOD OF IDENTIFICATION

FIELD OF THE INVENTION

This invention relates to building construction or remodeling materials that are identifiable through analysis of tagging material that naturally occurs in a binder, filler or other component of the building material.

BACKGROUND OF THE INVENTION

In the construction of buildings, one of the most common elements is gypsum wallboard, often known as drywall, used in the construction of walls and/or ceilings. One reason for the low cost of wallboard panels is that they are manufactured by a process that is fast and efficient. A slurry, including calcium sulfate hemihydrate and water, is used to form the core, and is continuously deposited on a paper cover sheet moving beneath a mixer. A second paper cover sheet is applied thereover and the resultant assembly is formed into the shape of a panel. Calcium sulfate hemihydrate reacts with a sufficient of the water to convert the hemihydrate into a matrix of interlocking calcium sulfate dihydrate crystals, causing it to set and to become firm. The continuous strip thus formed is conveyed on a belt until the calcined gypsum is set, and the strip is thereafter cut to form boards of desired length, which boards are conveyed through a drying kiln to remove excess moisture. Since each of these steps takes only minutes, small changes in any of the process steps can lead to gross inefficiencies in the manufacturing process.

Walls made from gypsum wallboard are conventionally constructed by affixing the panels to studs or joints and filling and coating the joints with a specially prepared adhesive called a joint compound. This process generally proceeds by placing a taping grade joint compound within the joint formed by the abutted edges of the wallboards and embedding a liquid-permeable tape within the taping compound. When dry (or set), a second coating comprising a topping grade joint compound is applied over the joint. This may be sanded lightly, then a third coat applied and conventionally finished. Another grade of joint compound is an all-purpose grade that may be used both for embedding the tape and for applying the finish coats. A patterned effect may be given to the finished wall and joint with the all-purpose joint compound to provide a textured finish.

There are two types of joint compounds that are commonly used. Compounds of the drying type become hard when the water evaporates. Setting type joint compounds become solid upon the absorption of water. Ready-mix formulations of setting type joint compounds often contain retarders to prevent the absorption of water during the shelf life of the product. When it is desirous to use the joint compound, it then becomes necessary to add an accelerator in order to overcome the effects of the retarder.

Drywall joint compounds may be sold either as a dry powder to be mixed with water, or in the form of a ready-mix compound. There are advantages to the ready-mix formula where it is inconvenient to provide or measure the water to be added at the job site. Additives are used in all types of joint compounds to modify physical and chemical properties of the compound to suit particular purposes.

When customers encounter a problem with a product, they call a manufacturer of that product to report the defect. If the wallboard or joint compound is applied by a contractor, as is often the case, the homeowner may not know what brand of building material has been used. Even if the homeowner does the work himself, he does not always save the label, container or other product identification. In these cases, it is not unusual for the homeowner to talk to a manufacturer with whom they are familiar, without being certain that the manufacturer actually made the gypsum-based building material installed in the owner's home. The manufacturer then spends a significant amount of time investigating the source of the product about which they received a complaint. Often, they find that the product is that of another manufacturer and that the time spent on the investigation was wasted. Manufacturers of such products have a need for a way of quickly and easily determining whether they actually made the joint compound that has been called into question.

A number of other compositions are used in building construction or remodeling products. These include, but are not limited to, plaster, textures, poured flooring, acoustical products and fiberboard. Any of these compositions are susceptible to questions of identification if a homeowner is unsatisfied with the product performance.

SUMMARY OF THE INVENTION

At least one of these or other problems is reduced using a building material that is uniquely identifiable. A method of making an identifiable gypsum-based building product includes selecting a tagging material occurring naturally in a component of the building material and choosing a carrier substance having a high concentration of the tagging material. By selecting an amount of the carrier substance and adding it to the building material, a building product having a unique product characteristic is created.

In a second embodiment of the invention, a second tagging material is combined with the first tagging material to create a unique product. Use of two tagging materials makes the unique product characteristic more specific. In yet another embodiment of the invention, a supplemental amount of the tagging material is added to the gypsum-based composition in addition to the carrier substance.

Some tagging materials are useful in a gypsum-based composition to produce a visual confirmation of the presence of the tagging material. The tagging material is added to a gypsum-based composition which is used to prepare a gypsum-based product. The product is then analyzed in situ to confirm the presence of the tagging material by application of an activator solution. In some embodiments, the activator solution is an oxidizing or reducing agent.

A method of using the building product made by the methods above includes analyzing the gypsum-based building composition by known methods and comparing that analysis to the known unique product characteristic to verify that the tagging material is present in appropriate amounts.

The method of making and using the subject gypsum-based building material allows the manufacturer of these building materials to easily and reliably analyze a sample of the building material to determine if the sample was made by the manufacturer. This saves time and countless analysis steps merely to determine whether a product with which a customer is unsatisfied belongs to the manufacturer in question.

DETAILED DESCRIPTION OF THE INVENTION

Where there is a possibility of having to identify a joint compound as originating with a particular manufacturer, it is advantageous to use a tagged joint compound. It is to be understood that the methods described below are applicable to any gypsum-containing building material, including wallboard, plasters, texturing products, acoustical products, poured floorings and the like. The methods also apply to building materials having no gypsum. An example of a non-gypsum building material is a drying-type joint compound. Additional examples of building materials are those that include calcium carbonate, cement and polymeric binders, in combination with each other or with gypsum. In some embodiments, the building materials are normally used for the preparation and finishing of walls, ceilings and floors. In the discussion below, a joint compound is used as an exemplary building material, but the methods are generally applicable to any building material.

Tagging of the joint compound occurs during product manufacture, when a tagged filler is added to a base joint compound composition. This invention may be used with any type of ready-mix joint compound that could benefit from addition of a premeasured additive at the time the joint compound is used. Both setting type and drying type joint compounds could be used in the product of this invention. The joint compound generally comprises a binder, fillers and additional, ready-mixed additives suitable for the particular application. The ready-mixed additives may include fillers, pigments, thickeners, preservatives, wetting agents, clays, polymers and surfactants.

The tagging material is an impurity that occurs naturally in stucco or one if the fillers and is easily identifiable by analysis. Use of a naturally occurring tagging material decreases the likelihood of interaction between the tagging material and other components of the joint compound. The tagging material is added to the gypsum in amounts that rarely occur naturally. Elements or compounds are both useful as tagging materials. When elements are used, the total amount of the element is obtainable by using one or more compounds using that include that element. In some embodiments, the tagging materials are elements in the form of salts that easily ionize into two or more elements in aqueous solution.

Examples of particularly useful elements are those that are naturally present in fillers or binders of joint compounds. In some embodiments, elements for tagging include, but are not limited to antimony, barium, beryllium, bismuth, chromium, cobalt, copper, molybdenum, nickel, selenium, silver, thallium, vanadium, and zinc. Sulfates and carbonates of these elements are particularly advantageous. These elements are present as elements or compounds in calcium carbonate, clays, mica, perlite, pigments and talc, each of which are known as raw materials for use in joint compounds. Selection of raw materials that include the tagging material effectively provides the tagging material free of cost. If the tagging material is considered to be an impurity, the price of the raw material may be less than raw materials having higher purity.

Table I shows several elements useful as tagging materials for joint compounds and the range of amounts naturally occurring in joint compound additives. Sources for these elements include fillers, clays and pigments. Calcium carbonate is a filler used extensively in drying-type joint compounds. The calcium carbonate has compounds that have many if these elements. Clays are added to joint compounds to modify the working time and to give the joint compound a smooth, creamy texture. Pigments give the joint compound its color, usually white. The tagging material is present in at least one of these joint compound additives in some embodiments of the invention.

This table also shows that the amounts of the various elements vary widely. In some cases, such as antimony and selenium, a unique product characteristic when a few parts per million of the tagging material is present. When using other tagging materials, such as barium and zinc, more of the tagging material is needed to make a unique formulation. As they occur naturally in the carrier substances, some of the tagging materials have few detrimental effects in the gypsum-based composition. The amount of the tagging material can range from about 1 ppm to about 10%, or even higher, of the gypsum-based composition.

TABLE I

| Element | Range, mm/kg (ppm) |
| --- | --- |
| Antimony | 0-4.31 |
| Barium | 0-596 |
| Beryllium | 0-121 |
| Bismuth | 0-0.99 |
| Chromium | 0-171 |
| Cobalt | 0-34.4 |
| Copper | 0-96.6 |
| Molybdenum | 0-22.2 |
| Nickel | 0-71.3 |
| Selenium | 0-3.7 |
| Silver | 0-1.62 |
| Thallium | 0-1.91 |
| Vanadium | 0-120 |
| Zinc | 0-840 |

Optionally, a supplemental amount of the tagging material is added to the gypsum-based composition to further increase the total amount of the tagging material. This serves at least two purposes. First, by increasing the amount of the tagging material, the sensitivity of analytical equipment needed to detect it can be reduced. Additionally, using the combination of the tagging material from natural and purified sources allows for additional unique product characteristics that cannot be found in nature alone.

The tagging material is contributed by two or more additives in another embodiment of the invention. If the element barium is selected as the tagging material, for example, it could be added as barium sulfate present in a calcium carbonate filler, as well as a compound in a sepiolite clay. The total amount of barium could exceed that normally present in this combination of additives, making it detectable as a product identifier.

In at least one embodiment of the invention, a second tagging material, different than the first tagging material, is also employed in the joint compound. The second tagging material does not naturally occur with the first tagging material, making it highly unlikely that the combination of the first tagging material and the second tagging would occur except by design. Any elements or compounds capable for use as the first tagging material are also useful as the second tagging material. Exemplary combinations of tagging materials include elemental barium in the form of barium carbonate and copper in the form of copper sulfate. These elements are unlikely to be present together in high concentrations in a natural filler.

The second component of the present invention is a base joint compound. The term "base joint compound" is used to refer to any joint compound prior to the addition of the additive containing the tagging material. Either setting or drying type joint compounds are suitable, although the results will be more evident in a base joint compound of the drying type. Both dry powder formulas, where water is added at the time of use, or ready-mix formulations, with the water mixed in at the time of manufacture, are suitable for use with this invention. It is also contemplated that the present invention will be used with lightweight formulations as well as traditional base joint compounds.

The base joint compound generally includes one or more binders, one or more fillers and other additives as required by the particular application to be used. Any conventional binder that is used in joint compounds may be utilized in this invention. Binders that are particularly suitable include polyvinyl acetates, acrylics, polyvinyl alcohols, redispersible powders, such as polyvinyl acetate, ethylene vinyl acetates, and starches. Latex binders are the preferred binders. Examples of suitable latex emulsion binders include ethylene vinyl acetate copolymer latex or polyvinyl acetate latex. Combinations of binders are also contemplated.

Certain fillers will be present depending on the type of joint compound to be prepared. Setting-type joint compounds are generally based on calcium sulfate hemihydrate, also known as stucco, calcined gypsum or Plaster of Paris. In the case of a setting-type joint compound, the stucco also acts as both the filler and the binder by forming an interlocking matrix of calcium dihydrate crystals as it sets. Drying-type joint compounds generally include either calcium carbonate or calcium sulfate dihydrate, also known as gypsum or landplaster, as fillers. The preferred filler is finely ground calcium carbonate. It is a dry powder that usually comprises at least about 50% by dry weight of the joint compound composition and generally falls within the range of about 50-95% of the dry weight. The ratio of the fillers to the binders is preferably in the range of about 100:1 to about 10:1.

Other fillers, such as perlite, expanded perlite, magnesium carbonate, glass or resin microbeads are also suitable fillers, depending on the type of joint compound desired. Dolomite, a mixture of calcium carbonate and magnesium carbonate, is also a preferred filler. Perlite or expanded perlite is preferred when a lightweight filler is desired. Often, several different fillers are used in combination to obtain a specific set of properties. Use of expanded perlite in a lightweight joint compound is taught in U.S. Pat. No. 4,454,267, which is herein incorporated by reference. Expanded perlite is a very lightweight material that contains many cracks and fissures. It is preferably treated according to the teachings of U.S. Pat. No. 4,525,388, which is hereby incorporated by reference, so that the material does not increase in weight due to water absorbed by capillary action. The treated, expanded perlite is preferably present in amounts of from about 8% to about 18% based on the dry weight. Lightweight fillers, as used in joint compounds, are taught in U.S. Pat. No. 4,454,267, filed Dec. 20, 1982, for a Lightweight Joint Compound, which is herein incorporated by reference. A combination of resin microbeads and expanded perlite is the preferred filler for lightweight joint compounds.

Thickeners are optionally added to the joint compound to achieve a desired consistency. Cellulosic compounds, associative thickeners or starches are the preferred thickeners, with cellulosic thickeners being most preferred. Conventional cellulosic thickeners, such as ethylhydroxy ethylcellulose, hydroxypropyl methylcellulose, methylhydroxypropyl cellulose and hydroxyethyl cellulose, are also suitable in the joint compounds of this invention. The amount of cellulosic thickener ranges from about 0.05% to about 2% of the weight of the total joint compound ingredients, excluding water.

Preservatives are optionally added to ready-mix formulations to prevent bacteria and fungi from attacking the organic components over a period of time. Both a bactericide and a fungicide are recommended. TROYSAN® 174 by Troy Chemical Company is the bactericide of choice, while the preferred fungicide is FUNGITROL® 158, made by Huls America, Inc. These ingredients are used in minor amounts, generally ranging from about 0.05 to about 1% of the total dry weight.

Finally, suspending agents are preferably included to keep the heavier components of the composition from settling out. Clays, such as bentonite, kaolin, sepeolite or attapulgite clay are particularly preferred suspending agents, with attapulgite clay being the most preferred. Suspending agents are generally present in amounts from about 0.5% to about 5% of the dry weight.

Water is added to the joint compound at the time of manufacture or just before use to achieve the correct viscosity. Generally, water is added to the joint compound until the desired viscosity is obtained, depending on the specific application for which it is used. Preferably, water is added until the Brabender viscosity reaches 350-850. A Brabender viscosity of 350-550 is most preferred when the viscosity is measured at the mixer. For ready-mix joint compound, viscosity of the final product as packaged will vary greatly depending on final product processing. Down-stream handling of the product often results in an increase in viscosity. The target viscosity of the packaged ready-mix product is preferably from about 400-700 Brabender units.

A set preventer is added to the setting-type ready-mix product to stop the hydration reactions. This prevents premature hardening of the product prior to application by the end user. A set initiator is often packaged with the ready-mix joint compound to overcome the effects of the set preventor and allow the hydration reactions to resume. Known set preventers include suma retarder and citric acid. Examples of the set initiator are zinc sulfate and aluminum sulfate A number of optional ingredients are also suitable to optimize the formulation for a particular application. Pigments are added to control the color of the finished joint compound. Mica or talc optionally is also added to the joint compound to modify the rheology of the slurry.

Manufacture of the ready mixed joint compound includes combining of wet with dry components in a mixer. Some ingredients are available in either dry or liquid form. The preferred binder, a latex binder, is a liquid, but other binders are available as powders. All components, including the tagging material, are grouped as to their physical form. The wet components are generally blended directly in the mixer. Water is placed in the mixer and first blended with the other wet components, such as the surfactant additive and the binder, if they are in liquid form. The dry components generally include the fillers, suspending agents and thickeners. If provided as a powder, the binder is also mixed with the dry components. These components are blended together before addition to the mixer using any technique known in the art to blend dry ingredients together. Powder feeders are optionally used to disperse the suspending agents or thickeners in with the fillers as they are moved to the mixer by conveyor.

After the wet ingredients have been combined, the dry components are mixed in with the wet components in the mixer. Mixing continues until a homogeneous mixture is obtained. Additional water is added, if necessary, to achieve a desired viscosity. This viscosity will vary depending on exactly what type of joint compound is being prepared, but the target viscosity is generally between 350-850 Brabender units.

When confirming the manufacturer of a joint compound having an tagging material, a sample of the joint compound is obtained and analyzed. Presence of the tagging material can be verified by If the sample analysis fails to verify the presence of the binder and one or more of the tagging materials in appropriate amounts, then the sample cannot be a product of that manufacturer. Where the testing verifies that the appropriate amounts of filler and tagging materials, additional testing may be needed to confirm that the sample is definitely made by the same manufacturer.

Other building materials are made by conventional methods except that carrier substance and the optional additional tagging materials are included in the gypsum-based composition. The carrier substance and tagging material are advantageously added at the same process step where the component corresponding to the carrier substance would normally be added. For example, if the carrier substance were a filler, it would be added where fillers would normally be added for the intended gypsum-based building product. Gypsum board products and their manufacture are described in U.S. Pat. No. 6,893,752. U.S. Pat. Nos. 5,320,677 and 7,413,603 are directed to the use and manufacture of fiberboard products. Gypsum-based flooring products are revealed in U.S. Pat. Nos. 7,056,964 and 7,504,165. Each of the previous five patents is incorporated by reference into this application in its entirety.

Analysis of the sample can be accomplished by any method that recognizes the tagging material. Mass spectroscopy, gas or liquid chromatography, infrared spectroscopy, X-ray diffraction, atomic absorption spectroscopy, inductively coupled plasma spectroscopy, X-ray fluorescence or any other method of analysis may be used. In some embodiments of the invention, the tagging material is selected, in part, because of the ability to be identified by a quick and inexpensive analysis. The analysis verifies the presence of the tagging material in amounts in excess of the expected dosage.

A field test is also useful in analyzing a sample to confirm the presence of a tagging compound. In this embodiment, the sample analysis is carried out in situ with the tagged building materials left in place. The tagging materials in this case are optionally, but are not necessarily, naturally occurring in the carrier substance of the gypsum-based composition. If not added with a carrier substance, the tagging material is added to any compatible component or added directly to a mixture of components of the gypsum-based composition.

Iodine is not normally considered as a tagging compound due to its intense color. However, when converted into a colorless compound, such as an iodate or an iodide compound, it can be used as a very useful tagging compound. The analysis then includes converting a portion of the iodine compound in the building material into elemental iodine, producing a visual confirmation of the presence of the tagging material. The minimum amount of tagging material is that amount that produces a visual confirmation. As iodates and iodides are colorless and inert, there is no specific limit as to a maximum useful amount. However, as a practical matter, the decrease in the other building product components will eventually cause it to loose adhesion and cease to function as a building product. One range for the amount of tagging material is from 0.05% to about 10 wt %. A more conservative range is from about 0.1% to about 5% iodate or iodide compound by weight. Preferred tagging materials include $K(IO_3)$, $Ca(IO_3)_2$, $KI$, $NaI$, $CaI_2$ and $Na(IO_3)$.

An activator, such as a liquid oxidizing or reducing agent, is used to create a color change of the building material in situ. When iodate compounds are used for tagging, reducing agents such as sodium sulfite are used. Iodide compounds are converted into iodine upon the addition of an oxidizing agent such as hydrogen peroxide ($H_2O_2$), sodium percarbonate or equivalent oxidizers. Solid materials, such as sodium sulfite ($Na_2SO_3$), are dissolved in water to make a solution that is from 50% to 100% saturated. A 30% solution of hydrogen peroxide was useful as an oxidizer. Other useful activators include $NaOCl$ and $NaHSO_3$. The activator solution is applied to the building material. A sufficient amount of the solution should be absorbed by the building material to saturate a small area. Decomposition of the iodine compounds changes the iodine from colorless in compound form to the characteristic reddish brown of elemental iodine.

The following examples demonstrate specific embodiments of this invention. They are not intended to define or limit the scope of the invention in any way.

EXAMPLE 1

A joint compound was prepared using calcium carbonate that included elemental barium as the tagging material. The components of Table II were obtained and assembled.

TABLE II

Components for Test Samples

| Raw Material | Source | Function | Concentration of Barium, ppm |
|---|---|---|---|
| Mica P 80 F | USG Corp., Chicago, IL | Pigment | 596 |
| Grefco HP 2000 | Grefco Minerals Inc., Bala Cynwyd, PA | Perlite | 84 |
| IGS | IMV Nevada, Amargosa Valley, NV | Clay | 84 |
| Mecellose FMC 53001 | Sumsung Fine Chemicals, Seoul, Korea | Thickener | 0 |
| ADF 1400 | Arizona Oxides, LLC, El Mirage, AZ | Pigment | 456 |
| Barium sulphate | | Tagging material | |
| Marblewhite 310 | Specialty Minerals Inc., Bethlehem, PA | Filler | 8.6 |
| Fullatex PD 0722 | H. B. Fuller Co., Palatine, IL | Latex Emulsion | 0 |
| K Flex DP | Noveon Kalama, Inc., Seattle, WA | Plasticizer | 0 |
| Mergal 174 | Troy Corporation, Florham Park, NJ | Biocide | 0 |

Three samples were made using the components of Table I. They were combined according to the amounts of Table II. Barium sulfate, as a supplemental barium source, was added to samples B and C to verify that the barium level was detectable. In Sample JE-9246B, barium sulfate was added until the amount of barium was 5,000 mg/kg (5,000 ppm). Barium sulfate was added in amounts to bring the barium concentration to 10,000 mg/kg in Sample JE-9246C.

The joint compound was prepared by combining all of the dry components in amounts shown in Table III in the amounts of Table IV.

TABLE III

Composition of Test Joint Compound Samples

| | JE-9246A | | JE-9246B | | JE-9246C | |
|---|---|---|---|---|---|---|
| RAW MATERIALS | % | grams | % | grams | % | grams |
| Mica P 80 F | 1.58 | 7.90 | 1.58 | 7.90 | 1.58 | 7.90 |
| Grefco HP 2000 | 1.92 | 9.60 | 1.92 | 9.60 | 1.92 | 9.60 |
| IGS | 3.72 | 18.60 | 3.72 | 18.60 | 3.72 | 18.60 |
| Mecellose FMC 53001 | 0.50 | 2.50 | 0.50 | 2.50 | 0.50 | 2.50 |
| ADF 1400 | 0.03 | 0.15 | 0.03 | 0.15 | 0.03 | 0.15 |
| Barium Sulphate | | | 0.50 | 2.50 | 1.00 | 5.00 |
| Marblewhite 310 | 90.37 | 451.85 | 89.87 | 449.35 | 87.90 | 439.50 |
| Fullatex PD 0722 | 1.53 | 12.75 | 1.53 | 12.75 | 3.00 | 25.00 |
| K Flex DP | 0.20 | 1.00 | 0.20 | 1.00 | 0.20 | 1.00 |
| Mergal 174 | 0.15 | 0.75 | 0.15 | 0.75 | 0.15 | 0.75 |

Several samples were analyzed for barium sulfate. Analysis of several commercially available joint compounds was carried out in addition to the three samples generated above. The results of the analysis are shown in Table IV.

TABLE IV

Analysis of Several Joint Compounds for Barium Sulfate

| Barium Sulphate | Ppm |
|---|---|
| JE-9246A | 14 |
| JE-9246B | 2484 |
| JE-9246C | 4840 |
| USG AP | <1 |
| USG Plus 3 | <1 |
| Green Dot | 150 |
| Black Dot | 24 |
| TnT Lite | 179 |
| Red Dot | 96 |
| Proform Multi use | 179 |

The analysis of Table III shows that levels of certain elements or compounds, such as barium, can be used to identify the manufacturer of gypsum-based products, such as joint compounds.

EXAMPLE 2

A field test for the presence of a tagging material was conducted. Base joint compound was made to include an iodine tagging material. Several tagging materials and activators were tested at two dosages each to determine if a noticeable color change was obtained. Iodides tested include potassium iodide, sodium iodide and calcium iodide. The color change in the iodides was initiated using a 30% hydrogen peroxide solution as the activator. Potassium and calcium iodates were added to the product in other samples. Each of the iodates was tested with a saturated solution of sodium sulfate and sodium bisulfate.

Each of the tagging materials was added to a base joint compound at the two dosages shown in Table V. The joint compounds were then applied to a wall and allowed to dry. Several drops of the activator were applied to the tagged joint compounds. Of the seven combinations of tagging materials and activators, the only differences on a qualitative level were according to dosage. Results are shown in Table V.

TABLE V

| Amount of Tagging Material | Results |
|---|---|
| 0.1% | Very light yellow spot |
| 0.5% | Brownish/yellow/black/blue circular stain that spread from the point of contact with the activator solution |

The results of Table V demonstrate the ability of the iodine compound to produce a stain of elemental iodine as a visual confirmation of the source of a gypsum-based product. When the tagging material is present in the gypsum-based product in the range of 0.05% to 0.2% by weight, the color of the indicator is a light yellow. In the range of 0.2% to 0.5% by weight, the color is light tan. A brown to dark brown stain is obtained in the range of 0.5% to 2% by weight of the tagging material. When starch or a starch derivative, such as a rheology modifier, is present in the building product, the visual indication may turn blue or black depending on the concentration of the iodine-containing component.

While particular embodiments of the Tagged building material and method of identification have been shown and described herein, it will be appreciated by those skilled in the art that changes and modifications may be made thereto without departing from the invention in its broader aspects and as set forth in the following claims.

What is claimed is:

1. A method of making an identifiable gypsum-based building product, comprising:
   selecting a tagging material from the group consisting of $K(IO_3)$, $Ca(IO_3)$, $KI$, $NaI$, $CaI_2$ and $Na(IO_3)$;
   choosing a carrier substance and determining a concentration of said tagging material in said carrier substance;
   adding an amount of the carrier substance and a supplemental amount of said tagging material to the building product, said amount and said supplemental amount being selected to provide the tagging material in amounts which create a unique product characteristic.

2. The method of claim 1, wherein the unique product characteristic is a color change after the exposure to a color-change activator.

3. The method of claim 1, wherein the total amount of the tagging material in the joint compound is at least 0.5%.

4. The method of claim 1 wherein the carrier substance of said choosing step is a filler, a binder, a pigment or a clay.

5. The method of claim 1 wherein the amount of the tagging material is from about 0.05% to about 10% by weight based on the total weight of the dry components.

6. The method of claim 1 wherein the supplemental amount of tagging material is from about 100 ppm to about 1% by weight based on the weight of the dry components.

7. The method of claim 1 wherein said unique product characteristic is a visual indicator.

8. The method of claim 1, wherein the building product is a joint compound.

* * * * *